United States Patent [19]
Gonda et al.

[11] Patent Number: 6,075,154
[45] Date of Patent: Jun. 13, 2000

[54] METHOD OF PREPARATION OF 2,2'-BIS (DIARYLPHOSPHINO)-6,6'-BIS (TRIFLUOROMETHYL)-1,1'-BIPHENYL, TRANSITION METAL COMPLEX USING IT AS LIGAND, AND OPTICALLY ACTIVE 3-HYDROXYBUTANOIC ACID ESTER DERIVATIVE OR β-BUTYROLACTONE

[75] Inventors: Yoshiharu Gonda; Yoji Hori; Akio Yamaguchi; Toshimitsu Hagiwara, all of Hiratsuka, Japan

[73] Assignee: Takasago International Corporation, Tokyo, Japan

[21] Appl. No.: 09/124,791

[22] Filed: Jul. 30, 1998

[30] Foreign Application Priority Data

Jul. 31, 1997 [JP] Japan ................................. 9-237599

[51] Int. Cl.[7] ........................... C07D 305/12; C07F 9/52; C07C 69/66; C07C 69/76
[52] U.S. Cl. ............................. 549/328; 556/13; 560/51; 560/174; 568/16; 568/17
[58] Field of Search ............................. 549/328; 560/51, 560/174; 556/13; 568/16, 17

[56] References Cited

FOREIGN PATENT DOCUMENTS 4-210696  7/1992  Japan .

OTHER PUBLICATIONS

Masanao et al, Synlett, 11, pp. 827–829, 1991.

*Primary Examiner*—Ba K. Trinh
*Attorney, Agent, or Firm*—Kubovcik & Kubovcik

[57] ABSTRACT

A novel phosphine compound usable as a catalyst in various asymmetric synthetic reactions is disclosed. The compound is a 2,2'-bis(diarylphosphino)-6,6'-bis(trifluoromethyl)-1,1'-biphenyl of (1):

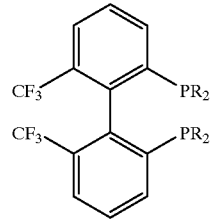

(1)

where R is a phenyl group or a phenyl group substituted by lower alkyl group, lower alkoxy group, halogen atom, or lower haloalkyl group.

11 Claims, No Drawings

METHOD OF PREPARATION OF 2,2'-BIS (DIARYLPHOSPHINO)-6,6'-BIS (TRIFLUOROMETHYL)-1,1'-BIPHENYL, TRANSITION METAL COMPLEX USING IT AS LIGAND, AND OPTICALLY ACTIVE 3-HYDROXYBUTANOIC ACID ESTER DERIVATIVE OR β-BUTYROLACTONE

BACKGROUND OF THE INVENTION

1. Field of the Invention

The present invention relates to a novel phosphine compound. More particularly, it relates to a novel phosphine compound which can be used as a useful catalyst in various asymmetric synthetic reactions by forming a complex with a transition metal such as rhodium, ruthenium, iridium, palladium and nickel. The invention further relates to a method for preparing chiral 3-hydroxybutanoic acid ester or chiral β-butyrolactone derived from acetoacetic acid ester or diketene by asymmetic hydrogenation, respectively.

2. Description of the Related Art

Numerous transition metal complexes usable in organic synthetic reactions such as asymmetric hydrogenation reactions or asymmetric isomerization reactions are known. In particular, the complex coordinating an optically active tertiary phosphine compound in a transition metal such as rhodium, ruthenium or palladium is disclosed to have an excellent performance as a catalyst in asymmetric synthetic reactions in many reports.

Among tertiary phosphine compounds, in particular, 2,2'-(diphenyl phosphino)-1,1'-binaphthyl (hereinafter called BINAP) is one of the excellent ligands, and, using this BINAP as a ligand, a rhodium complex (Japanese Patent Application Laid-open (JP-A) No. 55-61937) and a ruthenium complex (Japanese Patent Application Laid-open (JP-A) No. 61-6390) have already been reported. Moreover, it has also been reported that 2,2'-bis(dicyclohexylphosphino)-6,6'-dimethyl-1,1'-biphenyl (hereinafter called BICHEP), and 2,2'-bis(diphenylphosphino)-6,6'-dimethyl-1,1'-biphenyl (hereinafter called BIPHEMP) are effective ligands as catalysts in, respectively, asymmetric hydrogenation reactions of α,β-unsaturated carboxylic acids and carboxylic acid esters (Japanese Patent Application Laid-open (JP-A) No. 3-275691) and asymmetric isomerization reactions of allylamines (Japanese Patent Application Laid-open (JP-A) No. 63-135397).

However, numerous phosphine compounds developed for use as catalysts in such asymmetric synthetic reactions are not always sufficiently satisfactory in the aspects of selectivity, conversion ratio, optical purity, durability and the like depending on the intended reaction or reaction substrate to be used, and there has been a keen demand for development of a novel phosphine ligand for preparing a complex having a higher catalytic performance as compared with the conventional catalysts.

SUMMARY OF THE INVENTION

It is, therefore, an object of the invention to develop a novel phosphine ligand capable of obtaining sufficient effects with respect to selectivity, conversion ratio, optical purity and others in the intended reaction or reaction substrate to be used, and which forms a complex having a higher catalytic performance as compared with conventional catalysts as a catalyst for asymmetric synthetic reactions.

The present inventors intensively accumulated studies on tertiary phosphine compounds having axis asymmetricity in order to solve the above problems, and discovered that transition metal complexes such as rhodium, ruthenium and palladium using 2,2'-bis(diarylphosphino)-6,6'-bis (trifluoromethyl)-1,1'-biphenyl as a ligand are capable of enhancing the selectivity, conversion ratio, optical purity and other properties as compared with transition metal complexes using BINAP, BIPHEMP, BICHEP as ligands, and further continued the studies to complete the invention.

That is, the invention relates to a method for preparing 2,2'-bis(diarylphosphino)-6,6'-bis(trifluoromethyl)-1,1'-biphenyl and its derivative (hereinafter called BIRTFP) represented by formula (1)

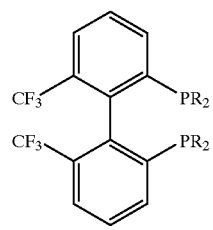

(1)

where R is a phenyl group or a phenyl group substituted with up to four groups selected from lower alkyl group, lower alkoxy group, halogen atom, or lower haloalkyl group, a transition metal complex using this BIRTFP as ligand and selected from the group consisting of rhodium complex, ruthenium complex, iridium complex, palladium complex, and nickel complex, and an optically active 3-hydroxy butyric acid ester derivative or β-butyrolactone characterized by asymmetrically hydrogenating an acetoacetic acid ester derivative or diketene in the presence of such transition metal complex.

In the compound (1), examples of the lower alkyl group include an alkyl group having 1 to 4 carbon atoms such as methyl group, ethyl group and propyl group, the lower alkoxy group includes an alkoxy group having 1 to 4 carbon atoms such as methoxy group, ethoxy group and propoxy group, preferred examples of the halogen atom include chlorine atom and fluorine atom, and examples of the lower haloalkyl group include trichloromethyl group and trifluoromethyl group.

The BIRTFP is manufactured, for example, according to the following reaction formula (1).

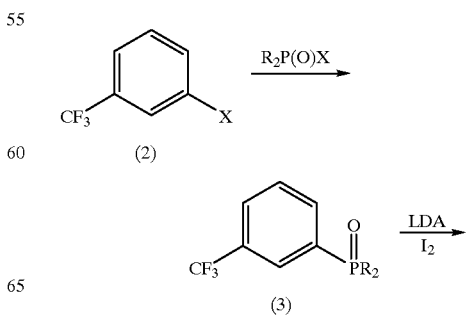

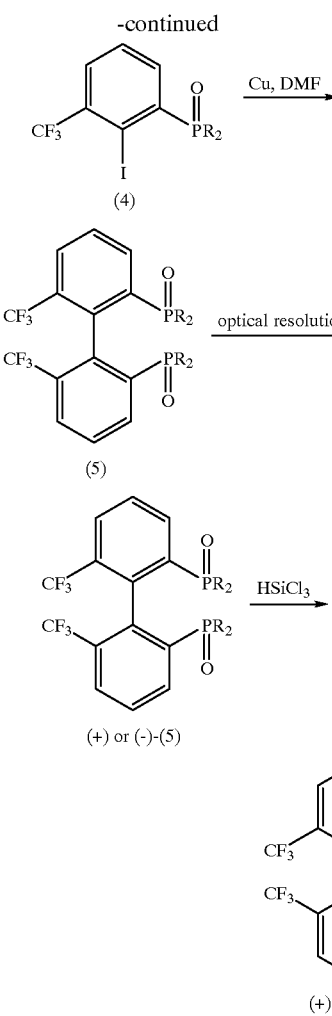

That is, 1-halo-3-trifluoromethyl benzene (2) is condensed with diarylphosphinyl halide in an inert solvent such as ether, tetrahydrofuran (hereinafter THF), toluene, or benzene, at a reaction temperature of −78° C. to 30° C., preferably −78° C. to 10° C., in the presence of metal magnesium or lower alkyl lithium, and 1-(diarylphosphinyl)-3-trifluoromethyl benzene (3) is obtained. The lower alkyl group in the lower alkyl lithium is an alkyl group having 1 to 4 carbon atoms, such as methyl group, ethyl group, propyl group, isopropyl group, normal butyl group, and isobutyl group. The aryl group of the diaryl phosphinyl halide is preferably a phenyl group without a substituent, or phenyl group substituted up to five groups selected from with lower alkyl group, lower alkoxy group, halogen atom, or lower haloalkyl group, and preferred examples include p-methoxy phenyl group, p-tert-butyl phenyl group, p-chlorophenyl group, p-tolyl group, 2,4-xylyl group, and p-trifluoromethyl phenyl group.

Compound (3) is made into a lithio form using a lithium alkyl amide, preferably lithium diisopropyl amide, at a reaction temperature of −78° C. to 30° C., preferably −78° C. to 10° C., in an inert solvent, such as ether, THF, toluene or benzene, and further, iodine is added into the reaction system, and 1-(diarylphosphinyl)-2-iodo-3-trifluoromethyl benzene (4) is obtained.

Compound (4), in the presence of copper powder, undergoes Ullman's coupling reaction in a non-protonic polar solvent such as dimethyl formamide, at a reaction temperature of 60° C. to 150° C., preferably 80° C. to 100° C., and racemic 2,2'-bis(diarylphosphinyl)-6,6'-bis(trifluoromethyl)-1,1'-bisphenyl (5) is obtained.

Using an optically active dibenzoyl tartaric acid as an optical resolution agent, recrystallization is repeated by employing the preferred recrystallization method from a mixed solvent of chloroform and ethyl acetate, and the racemate (5) is optically resolved. It is further treated in 1 N sodium hydroxide, and an optically pure compound is obtained. The optical purity is measured by high performance liquid chromatography using an optically active column (chiral cell OD-H, Daicel Chemical Industries, Ltd.).

The compound (5) of (−) form precipitates preferentially in the method of optical resolution using (−)-dibenzoyl tartaric acid, and the compound (5) of (+) form precipitates preferentially in the method of optical resolution using (+)-dibenzoyl tartaric acid.

When the obtained compound (5) of (+) form or compound (5) of (−) form is reduced by trichlorosilane, compound (6) of (+) form or compound (6) of (−) form is obtained.

By using the thus obtained BIRTFP, a complex is prepared together with a transition metal. Examples of transition metals for forming a complex include rhodium, ruthenium, iridium, palladium, nickel and the like. The formed complex includes the optically active complexes expressed, for example, in the following formulas (7), (8), (10), (12), (14), (15) and (16).

Optically active complex 1: $Ru_xH_yCl_z(BIRTFP)_2(A)_w$ (7)

In the formula, BIRTFP is (+)-BIRTFP or (−)-BIRTFP, A is a tertiary amine, and y is 0 or 1, and when y is 0, x is 2, z is 4, and w is 1, and when y is 1, x is 1, z is 1, and w is 0. Examples of the tertiary amine include triethylamine, tributylamine, ethyl diisopropylamine, 1,8-bis(dimethylamine)-naphthalene, dimethyl aniline, pyridine, N-methyl pyridine and the like. Triethylamine is preferred.

Practical examples of the optically active complex 1 include the following.

$Ru_2Cl_4(BIRTFP)_2NEt_3$ (where Et is ethyl group)

$RuHCl(BIRTFP)_2$

This optically active complex 1 is prepared using a method as disclosed, for example, in J. Chem. Soc., Chem. Commun., pp. 922–924 (1985), or Japanese Patent Application Laid-open (JP-A) No. 61-63690, incorporated herein reference. That is, it is produced when $[RuX_2(COD)]_q$ (where q is a natural number) obtained by the reaction of ruthenium chloride and cyclooctal-1,5-diene (hereinafter called COD) in ethanol solvent is heated to react with BIRTFP in the presence of the tertiary amine in a solvent such as toluene or ethanol.

Optically active complex 2: $[RuH_m(BIRTFP)_n]T_p$ (8)

In the formula, BIRTFP is same as above, T is $ClO_4$, $PF_6$ or $BF_4$, and m is 0 or 1, and when m is 0, n is 1 and p is 2, and when m is 1, n is 2 and p is 1.

Practical examples of the optically active complex 2 include the following.

$[Ru(BIRTFP)](ClO_4)_2$ $[Ru(BIRTFP)](PF_6)_2$ $[Ru(BIRTFP)](BF_4)_2$

[RuH(BIRTFP)₂]ClO₄

[RuH(BIRTFP)₂]PF₆

[RuH (BIRTFP)₂]BF₄

This optically active complex 2 is prepared using a method as disclosed, for example, in Japanese Patent Application Laid-open (JP-A) No. 63-41487 and Japanese Patent Application Laid-open (JP-A) No. 63-145292. For example, the compound of formula (8) where m is 0, n is 1, and p is 2 is prepared by reaction of Ru₂Cl₄(BIRTFP)₂NEt₃ in the optically active complex 1 and a salt of formula (9)

$$MT \qquad (9)$$

where M is a metal such as Na, K, Li or Ag, and T is the same as above, in a mixed solvent of water and hydrophobic organic solvent, in the presence of a quaternary ammonium salt or quaternary phosphonium salt as a phase-transfer catalyst, removing the hydrophobic organic solvent after termination of the reaction, and refining by distilling away the solvent and drying.

The hydrophobic organic solvent used herein includes methylene chloride, methylene bromide, toluene, and ethyl acetate, with methylene chloride being particularly preferred. The quaternary ammonium salt or quaternary phosphonium salt as a phase-transfer catalyst is not particularly limited and usual catalysts may be used. Preferred examples include tetramethyl ammonium fluoride, tetra(n-butyl) ammonium fluoride, tetra(n-butyl) ammonium chloride, tetra(n-octyl) ammonium chloride, benzyl tri(n-butyl) ammonium chloride, tetra(n-butyl) ammonium bromide, tetra(n-octyl) ammonium bromide, tetra(n-butyl) ammonium iodide, benzyl triphenyl ammonium chloride, tetra(n-butyl) phosphonium bromide, benzyl triphenyl phosphonium bromide, methyl triphenyl phosphonium iodide, and tetraphenyl phosphonium iodide. In particular, tetra(n-butyl) ammonium bromide, tetra(n-butyl) ammonium iodide, and tetra(n-butyl) phosphonium bromide are preferred.

The amount of the phase-transfer catalyst may be in an ordinary range, and, for example, it is used in an amount of 0.0001 to 0.2 mole, and preferably, 0.05 to 0.1 mole, per 1 mole of the optically active complex.

The reaction temperature is 0 to 50° C., preferably room temperature, and the reaction time is 3 to 48 hours, preferably 12 to 30 hours.

The compound in formula (8) where m is 1, n is 2 and p is 1 is prepared in the same manner as above by using RuHCl(BIRTFP)₂ as the optically active complex, the compound of formula (9), and the same phase-transfer catalyst.

$$\text{Optically active complex 3: } [RuX_a(Q)_b(BIRTFP)]L_c \qquad (10)$$

In the formula, BIRTFP is the same as above, X is a halogen atom (hereinafter it is not always indicated that X denotes a halogen atom), Q is acetonitrile or benzene which may have a substituent, L is a halogen atom, ClO₄, PF₆, BF₄ or BPh₄, and Ph is a phenyl group, and when Q is benzene which may have a substituent, a, b and c are all 1, or a and b are 1, and c is 3, or when Q is acetonitrile, a is 0 or 1, and when a is 0, b is 4 and c is 2, and when a is 1, b is 2 and c is 1.

The benzene which may have a substituent expressed by Q includes benzene or benzene substituted with up to six groups selected from lower alkyl group, lower alkoxy group, lower alkoxy carbonyl group, halogen atom or the like having a straight chain or branch chain having 1 to 4 carbon atoms, and practical examples include, among others, benzene, toluene, xylene, trimethyl benzene, hexamethyl benzene, ethyl benzene, tert-butyl benzene, p-cymene, cumene, anisole, methyl anisole, methyl benzoate, methyl methylbenzoate, methyl chlorobenzoate, chlorobenzene, dichlorobenzene, trichlorobenzene, bromobenzene, and fluorobenzene.

The halogen atom refers to chlorine atom, bromine atom, or iodine atom.

Practical examples of the optically active complex 3 include the following.

[RuCl(benzene)(BIRTFP)]Cl

[RuBr(benzene)(BIRTFP)]Br

[RuI(benzene)(BIRTFP)]I

[RuI(p-cymene)(BIRTFP)]I

[RuI(p-cymene)(BIRTFP)]I₃

[RuCl(methyl benzoate)₂(BIRTFP)]Cl

[RuCl(benzene)(BIRTFP)]ClO₄

[RuCl(benzene)(BIRTFP)]PF₆

[RuCl(benzene)(BIRTFP)]BF₄

[RuCl(benzene)(BIRTFP)]BPh₄

[Ru(acetonitrile)₄(BIRTFP)](BF₄)₂

[RuCl(acetonitrile)₂(BIRTFP)]Cl

The optically active complex 3 is obtained using a method disclosed, for example, in Japanese Patent Application Laid-open (JP-A) No. 2-191289, incorporated herein reference. That is, the compound in formula (10) where Q is benzene which may have a substituent and both X and L are halogen atoms is prepared by stirring [RuX₂(Q)]₂ and BIRTFP in a solvent until the solution is uniform, and distilling away the solvent and drying. The solvent used herein is methanol, ethanol, benzene, methylene chloride, and a mixed solvent thereof.

The reaction temperature is room temperature to 100° C., preferably the reflux temperature of the solvent used, and the reaction time is 3 to 48 hours, preferably 12 to 30 hours.

In particular, the compound in formula (10) where Q is p-cymene, X and L are iodine atoms, a and b are 1, and c is 3 is prepared by reaction of [RuI(p-cymene)(BIRTFP)]I and iodine in a solvent such as methanol, at 15 to 30° C. for 1 to 5 hours, and distilling away the solvent and drying.

The compound in formula (10) where Q is benzene which may have a substituent and L is ClO₄, PF₆, BF₄ or BPh₄ is prepared by reaction of a salt of formula (11):

$$ML^1 \qquad (11)$$

where M is the same as above, and $L^1$ is ClO₄, PF₆, BF₄ or BPh₄, in a solvent such as methanol, ethanol, benzene, or methylene chloride, at 15 to 30° C. for 1 to 5 hours, and distilling away the solvent and drying.

The compound in formula (10) where Q is acetonitrile, a is 1, b is 2, and c is 1 is prepared by dissolving, for example, [RuX(Q)(BIRTFP)]X in acetonitrile, heating to reaction at around 50° C., distilling away the solvent, and drying. The compound in formula (10) where Q is acetonitrile, a is 0, b is 4, and c is 2 is prepared by dissolving [RuX(Q)(BIRTFP)]X in a mixed solvent of acetonitrile and another solvent, and reacting them at 25 to 50° C., distilling away the solvent and drying. The other solvent used herein to be mixed with acetonitrile includes methanol, ethanol, acetone, methylene chloride, and the like.

Optically active complex 4: Ru(BIRTFP)J$_2$ (12)

In the formula, BIRTFP is the same as above, J is chlorine atom, bromine atom, iodine atom, or O$_2$CR$^1$, and R$^1$ is lower alkyl group or a halogen substituted lower alkyl group having 1 to 4 carbon atoms. Herein, the lower alkyl group is an alkyl group such as methyl group, ethyl group, propyl group, isopropyl group, n-butyl group, or isobutyl group, and the halogen substituted lower alkyl group is an alkyl group having a straight chain or branch chain having 1 to 4 carbon atoms, and substituted with up to nine halogen atoms, and specific examples include, among others, monochloromethyl group, dichloromethyl group, and trifluoromethyl group.

Practical examples of the optically active complex 4 include the following.

Ru(BIRTFP)Cl$_2$

Ru(BIRTFP)Br$_2$

Ru(BIRTFP)I$_2$

RU(BIRTFP)(O$_2$CCH$_3$)$_2$

RU(BIRTFP)(O$_2$CCF$_3$)$_2$

This optically active complex 4 is prepared, for example, by the following methods.

First, the compound in formula (12) where J is chlorine atom, bromine atom or iodine atom is prepared by a method disclosed, for example, in Tetrahedron Asymmetry, Vol. 2, No. 7, pp. 556–567 (1991), incorporated herein reference. That is, it is prepared by dissolving BIRTFP in a solvent, and adding a methanol solution of acid such as HCl, HBr, or HI to react. The solvent used herein includes methylene chloride, toluene, acetone, etc.

It is also prepared by a method of reacting Ru$_2$Cl$_4$(BIRTFP)$_2$NEt$_3$ of the optically active complex 1, and a salt of formula (13):

M$^2$L$^2$ (13)

where M$^2$ is a metal such as Na, K or Li, and L$^2$ is chlorine atom, bromine atom, or iodine atom, in a mixed solvent of water and hydrophobic organic solvent, in the presence of a quaternary ammonium salt or quaternary phosphonium salt as a phase-transfer catalyst, taking out the hydrophobic organic solvent after termination of the reaction, and distilling away the solvent and drying. This method is disclosed in "J. Am. Chem. Soc. 1987, 109, 5856", incorporated herein by reference.

The hydrophobic organic solvent used herein includes methylene chloride, methylene bromide, toluene, and ethyl acetate. Methylene chloride is particularly preferred. The quaternary ammonium salt or quaternary phosphonium salt as phase-transfer catalyst is not particularly limited and usual catalysts may be used. Preferred examples include tetramethyl ammonium fluoride, tetra(n-butyl) ammonium fluoride, tetra(n-butyl) ammonium chloride, tetra(n-octyl) ammonium chloride, benzyl tri(n-butyl) ammonium chloride, tetra(n-butyl) ammonium bromide, tetra(n-octyl) ammonium bromide, tetra(n-butyl) ammonium iodide, benzyl triphenyl ammonium chloride, tetra(n-butyl) phosphonium bromide, benzyl triphenyl phosphonium bromide, methyl triphenyl phosphonium iodide, and tetraphenyl phosphonium iodide, and, in particular, tetra(n-butyl) ammonium bromide, tetra(n-butyl) ammonium iodide, and tetra(n-butyl) phosphonium bromide are preferred.

The amount of the phase-transfer catalyst may be in an ordinary range, and, for example, it is used in an amount of 0.0001 to 0.2 mole and, preferably, 0.05 to 0.1 mole per 1 mole of the Ru$_2$Cl$_4$ (BIRTFP)$_2$NEt$_3$.

The reaction temperature is 0 to 50° C., preferably room temperature, and the reaction time is 3 to 48 hours, preferably 12 to 30 hours.

The compound of formula (12) where J is O$_2$CR$^1$ (R$^1$ is the same as above) is prepared by reacting, for example, a carboxylate including a group expressed as O$_2$CR$^1$ (R$^1$ is the same as above) with Ru$_2$Cl$_4$ (BIRTFP)$_2$NEt$_3$ in an alcohol solvent. The compound in formula (12) where J is a trifluoromethyl group is prepared by reacting, for example, Ru(BIRTFP)(O$_2$CCH$_3$)$_2$ with trifluoroacetic acid.

Optically active complex 5: RuG$_2$(BIRTFP) (14)

In the formula, BIRTFP is same as above, and G is allyl group or methallyl group.

Practical examples of the optically active complex 5 include the following.

Ru(C$_3$H$_5$)$_2$(BIRTFP) (where C$_3$H$_5$ is allyl group)

Ru(C$_4$H$_7$)$_2$(BIRTFP) (where C$_4$H$_7$ is methallyl group)

This optically active complex 5 can be also prepared by the same method as above. That is, according to the method disclosed in Tetrahedron Asymmetry, Vol. 2, No. 7, pp. 556–567 (1991), incorporated herein reference, it is prepared by reacting RuG$_2$ (COD) in the formula (where G is same as above) and BIRTFP in a solvent such as hexane in an atmosphere of argon at 50° C. for 3 to 48 hours by heating, distilling away the solvent, and drying.

Optically active complex 6: [M$^3$(D)(BIRTFP)]L' (15)

In the formula, BIRTFP is the same as above, M$^3$ is Rh or Ir, D is norbornadiene (NBD) or COD, and L' is ClO$_4$, PF$_4$, BF$_4$, or BPh$_4$ (where pH is a phenyl group).

Practical examples of the optically active complex 6 include the following.

[Rh(COD)(BIRTFP)]ClO$_4$

[Rh(COD)(BIRTFP)]PF$_6$

[Rh(NBD)(BIRTFP)]BF$_4$

[Rh(NBD)(BIRTFP)]BPh$_4$

[Ir(COD)(BIRTFP)]ClO$_4$

[Ir(COD)(BIRTFP)]PF$_6$

[Ir(NBD)(BIRTFP)]BF$_4$

[Ir(NBD)(BIRTFP)]BPh$_4$

The compound of optically active complex 6 where M$^3$ is Rh can be obtained by a method disclosed, for example, in J. Am. Chem. Soc., 93, 30, 89 (1971), incorporated herein reference. That is, it is prepared by reacting [Rh(D)$_2$]L' synthesized from [Rh(D)L']$_2$ with BIRTFP in methylene chloride at room temperature, and distilling away the methylene chloride in vacuo.

The compound of optically active complex 6 where M$^3$ is Ir can be obtained by a method disclosed, for example, in J. Chem. Soc. (A) 2334 (1971). That is, it is prepared by reacting [Ir(D)(CH$_3$CN)$_2$]L' with BIRTFP in methylene chloride at room temperature, and distilling away the methylene chloride in vacuo.

Optically active complex 7: M$^4$X'$_2$(BIRTFP) (16)

In the formula, BIRTFP is the same as above, M$^4$ is Ni or Pd, and X' is chlorine atom or bromine atom.

Practical examples of the optically active complex 7 include the following.

NiCl$_2$(BIRTFP)

NiBr$_2$(BIRTFP)

PdCl$_2$(BIRTFP)

PdBr$_2$(BIRTFP)

The compound in the optically active complex 7 where M$^4$ is Ni can be obtained in a method disclosed, for example, in J. Chem. Soc., 3239 (1965), incorporated herein reference. That is, it is prepared by adding an ethanol solution of BIRTFP to an ethanol solution of NiX'$_2$ to react, filtering the precipitating solid, and drying in a vacuum.

The compound in the optically active complex 7 where M$^4$ is Pd can be obtained by a method disclosed, for example, in J. Chem. Soc., 2537 (1962), incorporated herein reference. That is, it is prepared by reacting PdCl$_2$ and BIRTFP under reflux in ethanol, and distilling away the ethanol in vacuo.

In these optically active complexes 1 to 7, BIRTFP is used in either (+) form or (−) form. According to the invention, by selecting either the (+) form or (−) form, the optically active compound of a desired absolute configuration is obtained.

Incidentally, when using the optically active complex 5 as a complex catalytic component of an asymmetric hydrogenation reaction, it is preferred to add an acid properly selected from the group consisting of hydrochloric acid, trifluoroacetic acid and hydrobromic acid to the complex in the presence of a solvent such as acetone or toluene, and using the complex after distilling away the excessive acid or solvent in vacuo.

The thus obtained transition metal complexes are useful as a catalyst for the asymmetric hydrogenation reaction of various substrates. In particular, they can be used in asymmetric hydrogenation reactions of an acetoacetic acid ester derivative or diketene.

The acetoacetic acid ester derivative is represented by formula (17)

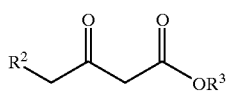
(17)

where R$^2$ is hydrogen atom or halogen atom, and R$^3$ is a straight chain or branched alkyl group having 1 to 4 carbon atoms or benzyl group which may have a substituent selected from a lower alkyl group having 1 to 4 carbon atoms, a lower alkoxy group having 1 to 4 carbon atoms, a nitro group and a halogen atom. Practical examples include methyl acetoacetate, t-butyl acetoacetate, benzyl acetoacetate, methyl 4-chloroacetoacetate, ethyl 4-chloroacetoacetate, etc. Commercial synthesized compounds can be used. For asymmetric hydrogenation of substrates, meanwhile, it is preferred to distill and treat before the asymmetric hydrogenation reaction.

By asymmetric hydrogenation of the acetoacetic acid ester derivative, an optically active compound represented by formula (18):

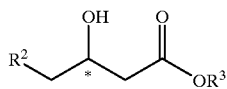
(18)

is obtained where R$^2$, R$^3$ are same as above, and * indicates an asymmetric carbon atom. Practical examples include optically active methyl 3-hydroxybutanoate, t-butyl 3-hydroxybutanoate, benzyl 3-hydroxybutanoate, methyl 4-chloro-3-hydroxybutanoate, and ethyl 4-chloro-3-hydroxybutanoate.

The diketene is a compound represented by formula (19):

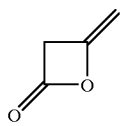
(19)

and a commercial synthetic compound can be used. For asymmetric hydrogenation of substrates, meanwhile, it is preferred to distill and treat before the asymmetric hydrogenation reaction.

By asymmetric hydrogenation of the diketene, an optically active β-butyrolactone represented by formula (20):

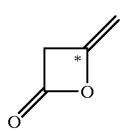
(20)

is obtained where * indicates an asymmetric carbon atom.

The asymmetric hydrogenation reaction is not particularly limited, but the following condition is preferred.

The amount of the transition metal complex used as the catalyst is 0.0001 mole to 0.01 mole, preferably, 0.0005 mole to 0.002 mole per 1 mole of the substrate.

The reaction catalyst is not particularly limited, and, for example, methylene chloride, acetone, methyl ethyl ketone, methyl butyl ketone, THF, 1,4-dioxane, ethyl acetate, butyl acetate, methanol, ethanol, isopropanol, t-butanol, benzene, and toluene can be used. The solvents may be used either alone or as a mixed solvent of two or more kinds.

The reaction temperature and reaction time of asymmetric hydrogenation reaction vary with the substrate, complex catalyst, solvent and other conditions being used, but usually at a temperature from room temperature to 100° C., the reaction continues for 1 hour to 50 hours. At this temperature, an appropriate hydrogen pressure is 5 to 100 kgf/cm$^2$.

EXAMPLES

The invention is more specifically described below in conjunction with examples and comparative examples, but it must be noted that the invention is not intended to be limited to these examples.

The following measuring system was employed to analyze the compounds obtained in the examples and comparative examples.

NMR: AM-400 (400 MHz) (Brucker Ltd.)

Standard substance $_1$H-NMR internal standard: tetramethyl silane $^{31}$P-NMR external standard: 85% phosphoric acid Angle of optical rotation: DIP-4 (Nippon Bunko Kogyo)

Example 1-a

Synthesis of 1-(diphenylphosphinyl)-3-trifluoromethyl benzene

In a nitrogen atmosphere, 24.5 g (109 mmol) of 1-bromo-3-trifluoromethyl benzene was dissolved in 200 ml of THF. This solution was cooled in a dry-ice-acetone bath, and 71.6 ml of 1.6 M:n-butyl lithium hexane solution was dropped for 1 hour. The dropping funnel was washed with 30 ml of distilled THF. The mixture containing the reaction solution and the washing was further stirred for 2 hours. In succession, a THF solution, 60 ml, containing 29.0 g (120 mmol) of diphenylphosphinyl chloride was dropped for 30 minutes in a dry-ice-acetone bath. After termination of dropping, the dropping funnel was washed with 30 ml of THF. The mixture containing the reaction solution and the washing was allowed to reach room temperature with further stirring, and the reaction solution was concentrated to 200 ml. Adding 200 ml of a 2 N: aqueous solution of sodium hydroxide, the organic phase extracted with THF and washed with a saturated brine. After drying with potassium carbonate, the dried extract was filtered and concentrated, and a brown oily matter was obtained. It was isolated in column chromatography (SiO$_2$ 350 g, CHCl$_3$/CH$_3$COOC$_2$H$_5$=6/1), and 14.56 g (45.5%) of the captioned compound in the form of pale yellow oily matter was obtained.

$^1$H-NMR(CDCl$_3$, δppm): 7.49 (dt, 4 H), 7.59 (dt, 2 H), 7.62 (dt, 1 H), 7.67 (dd, 4 H), 7.8 (d, 1 H), 7.84 (dd, 1 H), 7.99 (d, 1 H)

$^{31}$P-NMR(CDCl$_3$, δppm): 28.5(s)

Example 1-b

Synthesis of 1-(diphenylphosphinyl)-2-iodo-3-trifluoromethyl benzene

In a nitrogen atmosphere, 5.64 g (55.7 mmol) of diisopropylamine dehydrated by potassium hydroxide was dissolved in 50 ml of THF, and while cooling in a dry-ice-acetone bath, 30.2 ml (48.3 mmol) of 1.6 M:n butyl lithium hexane solution was dropped for 15 minutes.

Similarly, in a nitrogen atmosphere, in another reaction flask, 12.9 g (37.1 mmol) of 1-(diphenylphosphinyl)-3-trifluoromethyl benzene and 200 ml of THF were added and dissolved. This solution was cooled in a dry-ice-acetone bath, and 50 ml of THF solution of lithium diisopropyl amide (48.3 mmol) prepared the same as above was dropped for 1 hour. After stirring for 2 hours, 100 ml of a THF solution of 12.25 g (48.3 mmol) of iodine was dropped for 30 minutes. Stirring until reaching room temperature, an aqueous solution of sodium thiosulfate (Na$_2$S$_2$O$_3$ 3 g/H$_2$O 50 ml) and saturated brine were added, and the organic phase was extracted with THF. After drying with magnesium sulfate, the solvent was distilled away, and the residue was isolated by chromatography (SiO$_2$ 400 g, CHCl$_3$). After concentrating, to the obtained dark brown solid matter, 100 ml of THF and 50 ml of diisopropyl ether were added, and by cleaning in an ultrasonic cleaning apparatus, 8.11 g (46.2%) of the captioned compound in the form of pale yellow crystal was obtained.

$^1$H-NMR(CDCl$_3$, δppm): 7.29 (dd, 1 H), 7.41 (t, 1 H), 7.48 (dt, 4 H), 7.57 (dt, 2 H), 7.68 (dd, 4 H), 7.75 (d, 1 H)

$^{31}$P-NMR(CDCl$_3$, δppm): 35.5 (s)

Example 1-c

Synthesis of 2,2'-bis(diphenylphosphinyl)-6,6'-bis(trifluoromethyl)-1,1'-biphenyl In a nitrogen atmosphere, 4.16 g (8.81 mmol) of 1-(diphenylphosphinyl)-2-iodo-3-trifluoromethyl benzene was dissolved in 40 ml of dimethyl formamide, and 1.5 g of copper powder was added and stirred for 30 minutes at 100° C. After allowing to cool, dimethyl formamide was distilled away in vacuo, and the residue was refined by chromatography (SiO$_2$ 70 g, CHCl$_3$). By recrystallizing with ethyl acetate, 0.64 g (21%) of the captioned compound in the form of a white crystal was obtained.

$^1$H-NMR(CDCl$_3$, δppm): 7.16 (dt, 4 H), 7.28 (t, 2 H), 7.4 ( dt, 4 H), 7.45–7.62 (m, 14 H), 7.81 (d, 2 H)

$^{31}$P-NMR(CDCl$_3$, δppm): 30.6 (s)

Example 1-d

Optical resolution of 2,2'-bis(diphenylphosphinyl)-6,6'-bis(trifluoromethyl)-1,1'-biphenyl In 15 ml of chloroform and 5 ml of ethyl acetate, 0.69 g (1 mmol) of 2,2'-bis(diphenylphosphinyl)-6,6'-bis(trifluoromethyl)-1,1'-biphenyl and 0.395 g (1.05 mmol) of (−)-dibenzoyl tartarate monohydrate were dissolved by heating. After allowing to cool to room temperature, 0.40 g of precipitating crystal was filtered. This crystal was dissolved in 5 ml of chloroform, and 5 ml of 1 N aqueous solution of sodium hydroxide was added, and the solution was stirred for 14 hours at room temperature. After separating and extracting with chloroform, it was dried, the solvent was distilled away, and white crystal was obtained. The same operation was repeated until this crystal comes to show a constant degree of optical rotation, and 0.32 g of (−)-2,2'-bis(diphenylphosphinyl)-6,6'-di(trifluoromethyl)-1,1'-biphenyl was obtained.

$[\alpha]D_{25}$=−2.57° (c=0.7, CH$_2$Cl$_2$)

In the same operation, by using (+)-dibenzyl tartarate, (+)-2,2'-bis(diphenylphosphinyl)-6,6'-di(trifluoromethyl)-1,1'-biphenyl was obtained.

$[\alpha]D_{25}$=+2.56° (c=0.7, CH$_2$Cl$_2$)

Example 1-e

Synthesis of (−)-2,2'-bis(diphenylphosphino)-6,6'-bis(trifluoromethyl)-1,1'-biphenyl In 10 ml of xylene, 0.32 g (0.464 mmol of (−)-2,2'-bis(diphenylphosphinyl)-6,6'-bis(trifluoromethyl)-1,1'-biphenyl was dissolved. At room temperature, 0.42 g (2.78 mmol) of N,N-dimethyl aniline was added. While cooling the reaction solution at 0° C., 0.25 g (1.86 mmol) of trichlorosilane was added, and the solution was stirred for 30 minutes at room temperature, 1 hour at 100° C., 6.5 hours at 120° C., and 17 hours at 130° C. After allowing the reaction solution to cool to room temperature, 20 ml of 30% aqueous solution of sodium hydroxide was added. Extracting with toluene and washing with water, and drying, the solvent was distilled away. The obtained oily matter was recrystallized from ethanol, and 0.18 g of (−)-2,2'-bis(diphenylphosphino)-6,6'-bis(trifluoromethyl)-1,1'-biphenyl (hereinafter called (−)-BIFLUP) was obtained.

$^1$H-NMR(CDCl$_3$, δppm): 7.09–7.15 (m, 4 H), 7.15–7.24 (m, 10 H), 7.24–7.36 (m, 6 H), 7.48 (d, 4 H), 7.58 (t, 2H)

$^{31}$P-NMR(CDCl$_3$, δppm): −15.2(s)

$[\alpha]D_{25}$=−45.87° (c=1.09, CH$_2$Cl$_2$)

By using (+)-2,2'-bis(diphenylphosphinyl)-6,6'-bis(trifluoromethyl)-1,1'-biphenyl, in the same operation, (+)-2,2'-bis(diphenylphosphino)-6,6'-bis(trifluoromethyl)-1,1'-biphenyl (hereinafter called (+)-BIFLUP) was obtained.

$[\alpha]D_{25}$=+45.88° (c=1.09, CH$_2$Cl$_2$)

Example 2
Synthesis of Ru$_2$Cl$_4$((+)-BIFLUP)$_2$NEt$_3$

In a nitrogen stream, 0.08 g (0.121 mmol) of (+)-BIFLUP and 0.034 g (0.121 mmol) of RuCl$_2$(COD) were suspended in 10 ml of toluene, and 0.06 g (0.607 mmol) of triethylamine was added, and the solution was stirred for 8 hours at 130° C. until it was uniform. After distilling away toluene and an excess of triethylamine, it was dried in a vacuum at 50° C., and the complex was obtained.

Example 3
Synthesis of [RuCl(benzene)((−)-BIFLUP)]Cl

In a nitrogen stream, 0.1 g (0.152 mmol) of (−)-BIFLUP and 0.038 g (0.0759 mmol) of [RuCl$_2$(benzene)]$_2$ were suspended in 20 ml of methylene chloride and 13 ml of ethanol, and the solution was stirred for 23 hours at 50° C. until it was uniform. After distilling away the solvent, it was dried in vacuum, and the complex was obtained.

$^{31}$P-NMR(CDCl$_3$, δppm): 33.5 (d), 42.2 (d)

Example 4
Synthesis of [RuI(benzene)((+)-BIFLUP)]I

In a nitrogen stream, 0.1 g (0.152 mmol) of (+)-BIFLUP and 0.0657 g (0.0759 mmol) of [RuI$_2$(benzene)]$_2$ were suspended in 20 ml of methylene chloride and 30 ml of ethanol, and the solution was stirred for 96 hours at 50° C. until it was uniform. After distilling away the solvent, it was dried in vacuum at 50° C., and the complex was obtained.

$^{31}$P-NMR(CDCl$_3$, δppm): 32.8 (d), 39.6 (d)

Example 5
Synthesis of RuI$_2$((+)-BIFLUP)

In a nitrogen stream, 0.0546 g (0.031 mmol) of the complex obtained in Example 2 and 0.093 g (0.62 mmol) of sodium iodide were dissolved in 10 ml of methylene chloride. To this solution, a piece of tetrabutyl ammonium bromide, and 10 ml of water were added, and the solution was stirred for 2 hours at room temperature. After washing the methylene chloride phase three times in water, methylene chloride was distilled away. By drying in vacuum at 50° C., the complex was obtained.

Example 6
Synthesis of [Rh(COD)((+)-BIFLUP)]BF$_4$

In a nitrogen stream, 0.0057 g (0.00866 mmol) of (+)-BIFLUP and 0.00351 g (0.00866 mmol) of [Rh(COD)$_2$]BF$_4$ were dissolved in 20 ml of methylene chloride, and the solution was stirred for 2 hours at room temperature. After distilling away the solvent in vacuo, it was dried in a vacuum at 50° C., and the complex was obtained.

$^{31}$P-NMR(CDCl$_3$, δppm): 27.9 (s), 28.8 (s)

Example 7
Asymmetric hydrogenation of ethyl 4-chloroacetoacetate

In a stainless steel autoclave, 21 mg of sodium carbonate and 14.1 mg (0.008 mmol) of Ru$_2$Cl$_4$((−)-BIFLUP)$_2$NEt$_3$ were charged, and the air in the autoclave was replaced with nitrogen. Further, 6.6 ml of ethanol and 2.7 ml (20 mmol) of ethyl 4-chloroacetoacetate were added, and the nitrogen in the autoclave was replaced with hydrogen. At a hydrogen pressure of 10 kgf/cm$^2$, the solution was stirred for 2 hours at 100° C. After termination of the reaction, the conversion ratio, selectivity and optical purity were measured by gas chromatography and liquid chromatography. At a conversion ratio of 100%, selectivity of 96.3% and optical purity of 96.8%ee, ethyl 4-chloro-(S)-3-hydroxybutyrate was obtained.

Gas chromatography analysis conditions (measurement of conversion ratio, selectivity.

Column: NEUTRABOND-1 (G. L. Science, Ltd.)
Initial temperature: 100° C., rate 4° C./min
Injection temperature: 230° C.

Liquid chromatography analysis conditions (measurement of optical purity)
Eluate: Hexane/THF=97/3
Flow velocity: 1 ml/min
Detection wavelength: 254 nm

Example 8
Asymmetric hydrogenation of diketene

In a stainless steel autoclave, 54 mg (0.0595 mmol) of [RuCl(benzene)((−)-BIFLUP)]Cl was charged, and the air in the autoclave was replaced with nitrogen. Further, 35 ml of THF and 5 g (59.5 mmol) of diketene were added, and the nitrogen in the autoclave was replaced with hydrogen. At a hydrogen pressure of 100 kgf/cm$^2$, it was stirred for 26.5 hours at 50° C. After termination of the reaction, the conversion ratio, selectivity and optical purity were measured under the same gas chromatography conditions as in Example 8. At a conversion ratio of 100%, selectivity of 96.3% and optical purity of 95.5% ee, (S)-β-butyrolactone was obtained.

Example 9
Asymmetric hydrogenation of diketene

In a stainless steel autoclave, 129 mg (0.119 mmol) of [RuI(benzene)((+)-BIFLUP)]I was charged, and the air in the autoclave was replaced with nitrogen. Further, 35 ml of THF and 5 g (59.5 mmol) of diketene were added, and the nitrogen in the autoclave was replaced with hydrogen. At a hydrogen pressure of 90 kgf/cm$^2$, it was stirred for 22 hours at 50° C. After termination of the reaction, the conversion ratio, selectivity and optical purity were measured under the same gas chromatography conditions as in Example 8. At a conversion ratio of 100%, selectivity of 97.2% and optical purity of 94.8% ee, (R)-β-butyrolactone was obtained.

Comparative Example 1
Asymmetric hydrogenation of ethyl 4-chloroacetoacetate The same operation as in Example 7 was conducted except that 13.5 mg (0.008 mmol) of Ru$_2$Cl$_4$((R)-BINAP)$_2$NEt$_3$ was put in a stainless steel autoclave, and at a conversion ratio of 100%, selectivity of 95.9% and optical purity of 94.4% ee, ethyl 4-chloro-(S)-3-hydroxybutyrate was obtained.

Comparative Example 2
Asymmetric hydrogenation of ethyl 4-chloroacetoacetate In a stainless steel autoclave, 12.4 mg (0.008 mmol) of Ru$_2$Cl$_4$((R)-BIPHEMP)$_2$NEt$_3$ was charged, and the air in the autoclave was replaced with nitrogen. Further, 6.6 ml of ethanol and 2.7 ml (20 mmol) of ethyl 4-chloroacetoacetate were added, and the nitrogen in the autoclave was replaced with hydrogen. At a hydrogen pressure of 10 kgf/cm$^2$, it was stirred for 2 hours at 100° C. After termination of the reaction, the conversion ratio, selectivity and optical purity were measured under the same chromatography conditions as in Example 5. At a conversion ratio of 95.5%, selectivity of 93.9% and optical purity of 95.7%ee, ethyl 4-chloro-(S)-3-hydroxybutyrate was obtained.

Comparative Example 3
Asymmetric hydrogenation of diketene

In a stainless steel autoclave, 84.5 mg (0.05 mmol) of Ru$_2$Cl$_4$((S) BINAP)$_2$NEt$_3$ was charged, and it was replaced with nitrogen. Further, 28 ml of THF and 4.2 g (50 mmol) of diketene were added, and the autoclave was replaced with hydrogen. At a hydrogen pressure of 100 kgf/cm$^2$, it was stirred for 70 hours at 50° C. After termination of the reaction, the conversion ratio, selectivity and optical purity were measured under the same gas chromatography conditions as in Example 6. At a conversion ratio of 100%, selectivity of 98.4% and optical purity of 90.6% ee, (R)-β-butyrolactone was obtained.

Comparative Example 4
Asymmetric hydrogenation of diketene

In a stainless steel autoclave, 55.6 mg (0.05 mmol) of [RuI(benzene)((S)-T-BINAP)]I was charged, and it was replaced with nitrogen. Further, 28 ml of THF and 4:2 g (50 mmol) of diketene were added, and the autoclave was replaced with hydrogen. At a hydrogen pressure of 100 kgf/cm$^2$, it was stirred for 29.5 hours at 50° C. After termination of the reaction, the conversion ratio, selectivity and optical purity were measured under the same gas chromatography conditions as in Example 6. At a conversion ratio of 67.6%, selectivity of 99.2% and optical purity of 91.4% ee, (R)-β-butyrolactone was obtained.

Thus, the novel phosphine compound manufactured according to the invention is excellent as a ligand of a catalyst for asymmetric synthesis, and its complex with a transition metal has excellent catalytic activity. By using this complex as a catalyst for asymmetric synthesis such as asymmetric hydrogenation, a product of high optical purity can be obtained efficiently. The obtained optically active compounds are extremely useful as intermediate materials in the manufacture of organic synthetic polymer materials, pharmaceutical materials, liquid crystal materials, etc.

What is claimed is:

1. 2,2'-Bis(diarylphosphino)-6,6'-bis(trifluoromethyl)-1,1'-biphenyl of formula (1):

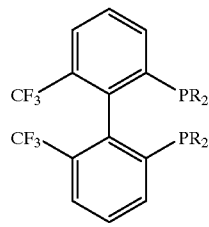

(1)

where R is a phenyl group or a phenyl group substituted with up to four groups selected from lower alkyl group, lower alkoxy group, halogen atom, or lower haloalkyl group.

2. A transition metal complex comprising the 2,2'-bis(diarylphosphino)-6,6'-bis(trifluoromethyl)-1,1'-biphenyl of claim 1 as ligand, and selected from the group consisting of a rhodium complex, ruthenium complex, iridium complex, palladium complex, and nickel complex.

3. A method of manufacturing an optically active 3-hydroxy butyric acid ester derivative of formula (18)

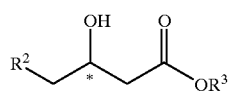

(18)

where R$^2$ is hydrogen atom or halogen atom, and R$^3$ is a straight chain or branched alkyl group having 1 to 4 carbon atoms or a benzyl group which may have a substituent selected from a lower alkyl group having 1 to 4 carbon atoms, a lower alkoxyl group having 1 to 4 carbon atoms, a nitro group and a halogen atom, and * indicates an asymmetric carbon atom, comprising asymmetrically hydrogenating an acetoacetic acid ester derivative of formula (17)

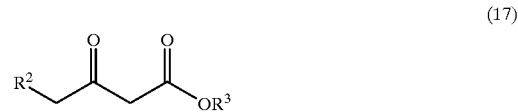

(17)

where R$^2$ and R$^3$ are defined as above, in the presence of the transition metal complex of claim 2.

4. A method of manufacturing an optically active β-butyrolactone comprising asymmetrically hydrogenating a diketene in the presence of the transition metal complex of claim 2.

5. A transition metal complex of claim 2, wherein said complex is

where BIRTFP is said 2,2'-bis(diarylphosphino)-6,6'-bis(trifluoromethyl)-1,1'-biphenyl, A is a tertiary amine, and y is 0 or 1, and when y is 0, x is 2, z is 4, and w is 1, and when y is 1, x is 1, z is 1, and w is 0.

6. A transition metal complex of claim 2, wherein said complex is

where BIRTFP is said 2,2'-bis(diarylphosphino)-6,6'-bis(trifluoromethyl)-1,1'-biphenyl, T is ClO$_4$, PF$_6$ or BF$_4$, and m is 0 or 1, and when m is 0, n is 1 and p is 2, and when m is 1, n is 2 and p is 1.

7. A transition metal complex of claim 2, wherein said complex is

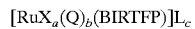

where BIRTFP is said 2,2'-bis(diarylphosphino)-6,6'-bis(trifluoromethyl)-1,1'-biphenyl, X is a halogen atom, Q is acetonitrile or benzene which may have a substituent, L is a halogen atom, ClO$_4$, PF$_6$, BF$_4$ or BPh$_4$, and Ph is a phenyl group, and when Q is benzene which may have a substituent, a, b and c are all 1, or a and b are 1, and c is 3, or when Q is acetonitrile, a is 0 or 1, and when a is 0, b is 4 and c is 2, and when a is 1, b is 2 and c is 1, and wherein each of said substituents is independently a lower alkyl group, lower alkoxy group, or lower alkoxy carbonyl group, where said lower alkyl is straight chain or branch chain having from 1 to 4 carbon atoms, or halogen atom.

8. A transition metal complex of claim 2, wherein said complex is

where BIRTFP is said 2,2'-bis(diarylphosphino)-6,6'-bis(trifluoromethyl)-1,1'-biphenyl, J is chlorine atom, bromine atom, iodine atom, or O$_2$CR$^1$, and R$^1$ is lower alkyl group having 1 to 4 carbon atoms or a halogen substituted lower alkyl group having 1 to 4 carbon atoms.

9. A transition metal complex of claim 2, wherein said complex is

RuG$_2$(BIRTFP)

where BIRTFP is said 2,2'-bis(diarylphosphino)- 6,6'-bis(trifluoromethyl)-1,1'-biphenyl, and G is allyl group or methallyl group.

10. A transition metal complex of claim 2, wherein said complex is

[M$^3$(D)(BIRTFP)]L' where BIRTFP is said 2,2'-bis(diarylphosphino)-6,6'-bis(trifluoromethyl)-1,1'-biphenyl, M$^3$ is Rh or Ir, D is norbornadiene (NBD) or COD, and L' is ClO$_4$, PF$_4$, BF$_4$, or BPh$_4$, where pH is a substituted or unsubstituted phenyl group.

11. A transition metal complex of claim 2, wherein said complex is

M$^4$X'$_2$(BIRTFP)

where BIRTFP is said 2,2'-bis(diarylphosphino)-6,6'-bis(trifluoromethyl)-1,1'-biphenyl, M$^4$ is Ni or Pd, and X' is chlorine atom or bromine atom.

* * * * *